United States Patent [19]
Kendall et al.

[11] Patent Number: 6,048,325
[45] Date of Patent: Apr. 11, 2000

[54] WRIST/HAND SUPPORT DEVICE

[76] Inventors: David W. Kendall, 1492 S. 900 West, Salt Lake City, Utah 84104; Craig L. Broadbent, 1520 N. Fort Canyon Rd., Alpine, Utah 84004; Bruce Y. Broadbent, 6348 W. 10570 North, Highland, Utah 84003; Randy K. Russon, 810 N. 1060 East, Lehi, Utah 84043

[21] Appl. No.: 08/968,603

[22] Filed: Nov. 13, 1997

Related U.S. Application Data

[63] Continuation-in-part of application No. 08/609,675, Mar. 1, 1996, Pat. No. 5,731,711.

[51] Int. Cl.[7] ............................... A61F 5/00; B43L 15/00
[52] U.S. Cl. ................... 602/21; 602/5; 248/118
[58] Field of Search ...................... 602/5, 70, 21, 602/64; 128/112.1, 113.1, 117.1, 118.1; 248/118, 118.1, 118.5

[56] References Cited

U.S. PATENT DOCUMENTS

| | | |
|---|---|---|
| 8,065 | 4/1851 | Goshon et al. . |
| 89,142 | 4/1869 | Gorsline . |
| 310,257 | 1/1885 | Cowan . |
| 520,711 | 5/1894 | Shea . |
| 793,756 | 7/1905 | Williams . |
| 1,510,877 | 10/1924 | Wiedenmann . |
| 1,627,635 | 5/1927 | Craig . |
| 2,644,449 | 7/1953 | Champagne . |
| 4,313,585 | 2/1982 | Bricker . |
| 5,165,630 | 11/1992 | Connor . |
| 5,265,835 | 11/1993 | Nash . |
| 5,270,692 | 12/1993 | Rockwell . |
| 5,335,888 | 8/1994 | Thomsen . |
| 5,439,192 | 8/1995 | King . |
| 5,445,349 | 8/1995 | Hart . |

*Primary Examiner*—Richard J. Apley
*Assistant Examiner*—Denise Pothier
*Attorney, Agent, or Firm*—Thorpe, North & Western, LLP

[57] ABSTRACT

A wrist support device including a modular body having an upper portion and a separate lower portion removably attachable to the upper portion. A glide mechanism, such as felt for lower friction surfaces or plastic for high friction surfaces is disposed in an indentation formed on a lower surface of the lower portion. Different lower portions may be provided with different glider mechanisms to suit the intended surface. The upper portion has an upper surface flexibly movable between a convex orientation and a concave orientation. The upper surface is biased in the convex orientation and facilitates separation between the skin of the wrist and the upper surface caused by sweat and oil. The upper portion has a perimeter wall surrounding the upper surface for biasing the wrist into a laterally inclined orientation and nesting the wrist into the approximate center of the upper surface. A cushion is disposed in a cavity formed between the upper and lower portions. The upper portion is moveably attached to the lower portion and moves between upper and lower positions to provide an initial stage of cushion, while the upper surface moves between convex and concave orientations to yield a second stage. The upper portion is also pivotally attached to the lower portion to pivot a small degree with the wrist.

30 Claims, 6 Drawing Sheets

WRIST/HAND SUPPORT DEVICE

This application is a continuation in part of application Ser. No. 08/609,675, filed Mar. 1, 1996 U.S. Pat. No. 5,731,711.

BACKGROUND OF THE INVENTION

1. Field of the invention

The present invention relates to a wrist support device and, in particular, to a device which is used to support the base of a user's hand and the bones of the wrist when performing repetitive motions, such as typing or data entry on a computer keyboard, thereby preventing the development of repetitive stress disorders, such as carpal tunnel syndrome.

2. Prior art

Due to the widespread use of computers and other word processing equipment, the number of persons using keyboards to enter data and perform other tasks which involve repetitive movements of the fingers and hands has greatly increased. With these increases in the number of users has also come an increased understanding of the risks which repetitive stresses raise regarding the health of those using such devices. The most common are repetitive stress disorders such as carpal tunnel syndrome—a disorder which can lead to debilitating pain in the wrists of those who use typewriters, keyboards and other data entry devices.

Carpal tunnel syndrome is believed to develop as the hands and wrists of the user are held in an unnatural position during repetitive tasks performed over a prolonged period of time which place stress on the wrist. The most common scenario is that of a secretary or data entry person who spends long hours entering information into a computer via the computer's keyboard.

To avoid the pain suffered by employees and the loss of valuable employee time which accompany repetitive stress disorders, several devices have been created to reduce the risk of persons getting carpal tunnel syndrome. One common device is a wrist support brace which is worn about the wrist and lower part of the user's hand. The wrist support brace has braces formed therein to prevent the wrist from bending and causing stress on the damaged or inflamed carpal tunnel within the wrist. However, such devices are generally not favored because they are inconvenient, time consuming and awkward to put on and to remove by oneself. Additionally, the braces restrict all movement of the wrist, may put pressure on the inflamed or damaged wrist, and are generally unsightly. Thus, the wrist support braces are generally only worn by those who are already suffering from wrist pain due to repetitive stress disorders.

Another device which has gained significant popularity is an elongate pad. The elongate pad is typically made of neoprene or some other somewhat pliable material and is positioned in front of the keyboard so that the user's hands or wrists may rest on the pad while typing. Unfortunately, the pad does not move with the user's hands or wrists. As a user moves his or her hands, the material of the elongate pad tends to irritate the skin on the bottom of the wrist as the two rub against one another. Those who work for prolonged hours using such a device often suffer pronounced irritation on the underside of the hand and wrist.

An additional concern with the elongate pads is that they can actually cause stress on the wrist. If the bony portion of the user's wrist (i.e. the portion including the pisiform) is placed above the pad, the lack of support under the other wrist bones, especially those near the base of the thumb, causes the user's hand/wrist to rotate into a generally horizontal position. The natural position for a persons hand/wrist is an incline of between 10 and 30 degrees. As the wrist and the user's hand are held in a horizontal position, the elbow is forced to rotate outwardly and additional stress is placed on the wrist, as gravity continually pulls down on the elbow.

To overcome these concerns, many users place the elongate pad directly below the soft tissue between the bones of the wrist and the radius and ulna, minimizing the amount of rotation. However, in such a position, the weight of the arms and hands places pressure on the soft tissues and on the tendons of the wrist. This, in turn, raises concerns of repetitive stress disorders.

While other suggestions have been made regarding the attachment of wrist supports to a user's arm, see e.g. U.S. Pat. No. 1,510,877, such devices are generally not desirable because they move with the user's hands when lifted away from the keyboard. Thus, for example, if the hands of a person periodically leave the keyboard to pick up or move materials, the support devices go with the user's hands, potentially interfering with the other task. Additionally, having a support device strapped to one's wrist is generally unattractive and restricts natural breathing and air circulation at the skin. Such unnatural conditions can be problematic for people with sensitive skin. Furthermore, if the strap is securely placed around the wrist, additional pressure would be applied to the carpel tunnel and actually increase the risk of repetitive stress disorders, rather than helping reduce the risk of the same.

Co-pending application Ser. No. 08/609,675, filed Mar. 1, 1996, provides a significant improvement over prior art devices by providing a wrist support means with an upper surface defining a concave portion configured to engage the pisiform of a user, a biasing means circumscribing the concave portion for biasing the wrist to a laterally inclined orientation and nesting the wrist into the approximate center of the upper surface, and a gliding means for movement of the wrist support means along a planar surface. Thus, the wrist of the user is encouraged into a natural orientation and moves planarly with the wrist of the user.

However, there is still a need for a device which supports the wrist of the user in a more cushioned manner. In addition, there is a need for such a device that will facilitate the release of the user's wrist from the surface of the device because natural adhesion occurs from prolonged contact. In addition, there is a need for a device capable of use with both low and high friction surfaces, including desks and mouse pads. In addition, there is a need for a device that provides different stages of cushion, or various levels of cushioning as engaged by the wrist. Furthermore, there is a need for a device that allows the wrist and hand to pivot or rotate a small amount for added comfort.

SUMMARY OF THE INVENTION

Thus, it is an object of the present invention to provide a wrist support device which supports the hand and bony portion of the user's wrist when typing or performing other similar repetitious movements of the fingers and hands to thereby relieve pressure on the user's wrist.

It is another object of the present invention to provide such a device which is movable with the user's wrists, both to the sides and forward and backward relative to the keyboard being used.

It is yet another object of the present invention to provide such a device which need not be attached to the user's hands, wrists or arms, so that the device may remain in place when the user's hands are drawn away from the keyboard, etc.

It is still another object of the present invention to provide such a device which can be easily configured to move along different planar support surfaces, such as a low friction desk or a high friction neoprene "mouse" pads.

It is still another object of the present invention to provide such a device which will easily move along planar support surfaces in a stable manner.

It is an additional object of the present invention to provide such a device which is easy to use and inexpensive to manufacture.

Another object of the present invention is to support the user's hands in a natural position so as to minimize stress on the user's wrists, and which provides a soft cushion to decrease tender areas on the wrist and hands causes by pressure from the weight of the arms.

Yet another object of the present invention is to provide such a device to receive a portion of the wrist under the pisiform (heel of the wrist), thereby forcing the user to properly position the device under the bones of the wrist rather than the soft tissue of the wrist.

A further object of the present invention is to provide such a device in which the portion of the wrist support which is commonly contacted by the user's hand and wrist may be readily sanitized with common cleaning chemicals.

Another objective of the present invention is to provide such a device to facilitate the release of the device from user's wrist after natural adhesion has taken place due to sweating following prolonged use.

Another objective of the present invention is to provide such a device that provides different degrees or stages of cushioning as the wrist engages the device.

Another objective of the present invention is to provide such a device that allows the wrist and hand to pivot or rotate a small degree for added comfort to facilitate the initial placement of the wrist in the device.

The above and other objects of the invention are realized in specific illustrated embodiments of a wrist support device including a modular wrist support body having an upper portion and a separate lower portion removably attachable to the upper portion. A glide mechanism for facilitating movement of the wrist support body along a planar surface is disposed on a lower surface of the lower portion. A cushion is disposed in a cavity formed between the upper and lower portions.

In accordance with one aspect of the invention, the upper portion has an upper surface which is formed of a flexible material which conforms to the shape of the projection formed by the bones of the user's wrist (commonly referred to as the heel of the hand), and in particular the pisiform, when the user's hand/wrist is placed thereon. The upper surface provides padding to the bones of the hand and wrist, and supports the hand and wrist in a position which relieves pressure on the soft tissue of the user's wrist. The upper portion also allows prolonged use without irritating the skin of the wrist or causing sore spots thereon.

In accordance with another aspect of the present invention, the flexible material frictionally engages the skin overlying the pisiform and extends below the lower hand and the soft tissue of the wrist. As the hand and wrist are moved laterally, toward, and away from the keyboard, the wrist support device moves with the user's hand and prevents the position of the hand from causing unnecessary pressure on the wrist. This prevents the damage caused by lack of support, but gives the user full range of movement. Additionally, because the wrist support devices move with the user's hands and wrists, they do not irritate the skin after prolonged use. Furthermore, because of the frictional engagement between the wrist supports and the user's wrists, the devices need not be attached to the user's wrists, as do many movable devices of the prior art. Thus, the user need not repeatedly attach and detach the wrist supports when periodically moving between use of the keyboard and other matters.

In accordance with an additional aspect of the present invention, the upper portion has an upper surface which is configured to conform to the bones which form the heel of the hand, and in particular the pisiform. The upper portion supports the wrist while preventing sore spots on the wrist, and holds the hand in a more natural position. Rather than forcing the hand to remain generally horizontal during typing, the configuration of the compressible pillow allows the fingers to strike the keys with little, if any, rotation and encourages the hand to remain in its natural position after the key stroke has been completed.

In accordance with another aspect of the invention, the upper portion has an upper surface flexibly movable between a convex orientation and a concave orientation. The upper surface is biased in the convex orientation when in a relaxed, or unused state. The biased, convex shape helps cushion the user's wrist and facilitates separation caused by adhesion between the user's skin and the upper surface due to sweat and oil. The upper surface moves to the concave orientation when engaged by the wrist of a user. The cushion cushions the wrist of the user and biases the upper surface in a convex orientation.

In accordance with another aspect of the invention, the upper portion has a perimeter wall surrounding the upper portion and biasing the wrist of the user into a more natural and comfortable laterally inclined orientation. The perimeter wall also nests the pisiform bone on the wrist in the concave shape of the upper surface.

In accordance with another aspect of the invention, the glide mechanism is in the form of a piece of soft material which may be repeatedly moved over a working surface, such as a desk, without marring the surface. In a preferred embodiment, the glide mechanism is formed of a piece of felt. Unlike balls or other materials of the prior art, the felt can be moved thousands of times across a work surface without marking or marring the surface. The material enables a person to use the device on surfaces for use with keyboards, a mouse, ten-keys, etc.

In accordance with yet another aspect of the present invention, the glide mechanism includes a piece of hard plastic which will glide across neoprene and other plastic or rubber-like materials with little friction. The material enables a person to use the device on pads used for a mouse or other pointer controlling devices which are designed to be high in friction.

In accordance with another aspect of the present invention, the material forming the upper portion is formed of polypropylene or other similar material which can be easily sanitized with conventional cleaning materials. If the wrist supports are used by several different people, the surface on which the user's wrist will rest can be conveniently sanitized after each use to prevent the transmission of unhealthy bacteria. If the wrist support is used by a single person, the wrist supports can be cleaned periodically, i.e. weekly, to prevent the build-up of stain or odors caused by perspiration.

In accordance with another aspect of the present invention, the body is modular and has separate and removable upper and lower portions. Different lower portions, with different glide mechanisms, may be attached to the upper portion to suit the intended surface. The upper portion has a cavity and an opening formed in a bottom of the upper portion. The bottom surrounding the opening forms a flange or lip. The lower portion also has a cavity and a notch formed in a perimeter wall. A portion of the perimeter wall of the lower portion passes through the opening in the upper portion and is received in the cavity of the upper portion. The notch of the lower portion mates with the flange of the upper portion to attach the lower portion to the upper portion.

In the preferred embodiment of the present invention, a gap is formed about the periphery of the device between the upper and lower portions. The gap allows the upper portion to move between an upper position, in a relaxed state, and a lower position, when engaged by the wrist of a user. The upper portion is biased in the upper position, thus creating the gap. The upper portion is moveably attached to the lower portion.

As the wrist of the user engages the upper surface of the device, the upper portion moves from the upper position to the lower position. This movement provides an initial stage of cushioning for the wrist. This movement is resisted by the cushion and air contained in the device. As the upper portion moves towards the lower portion, air is slowly released from the device through the gap.

In addition, the gap allows the upper portion to pivot a small degree with respect to the lower portion. Thus, the upper portion is also pivotally attached to the lower portion. As the wrist and hand of the user pivot or rotate, the upper portion pivots on the lower portion. This pivot provides the device with added flexibility and comfort without compromising the device's ability to bias the wrist in the proper orientation. In addition, the pivoting upper portion provides a small degree of forgiveness in the positioning of the pisiform in the center of the upper surface.

Furthermore, the gap allows air to escape from the device to equalize the pressure within the device. Thus, the device can provide comfort at various altitudes and even on aircraft.

In accordance with another aspect of the present invention, the lower portion has a lower surface. A ridge is formed around the perimeter of the lower surface to create an indentation. The glide mechanism is received in the indentation and the ridge helps position the glide mechanism in the appropriate position on the lower surface. The glide mechanism may be removably disposed in the indentation.

In accordance with another aspect of the present invention, a channel is formed about a periphery of the lower surface of the lower portion. The channel receives an edge of the glide mechanism. As the wrist or hand pivots or rotates, the edge of the glide mechanism bends into the channel, thus changing the planar nature of the glide mechanism and allowing the lower portion to pivot a small degree with respect to the surface. This small pivot allows the wrist and hand to pivot a small degree for added comfort.

By continued use of such a wrist support, it has been found that a significant decrease in fatigue and injury can be achieved for those who spend prolonged periods of time working on typewriters and computer keyboards. The user's wrists are fully supported without the skin irritation and other problems of the prior art. Additionally, the small size of the wrist supports make them more convenient for movement between computers for those who routinely work on keyboards at different locations.

BRIEF DESCRIPTION OF THE DRAWINGS

The above and other objects, features and advantages of the invention will become apparent from a consideration of the following detailed description presented in connection with the accompanying drawings in which.

DETAILED DESCRIPTION

Reference will now be made to the drawings in which the various elements of the present invention will be given numeral designations and in which the invention will be discussed so as to enable one skilled in the art to make and use the invention. It is to be understood that the following description is only exemplary of the principles of the present invention, and should not be viewed as narrowing the pending claims.

Figure 1:
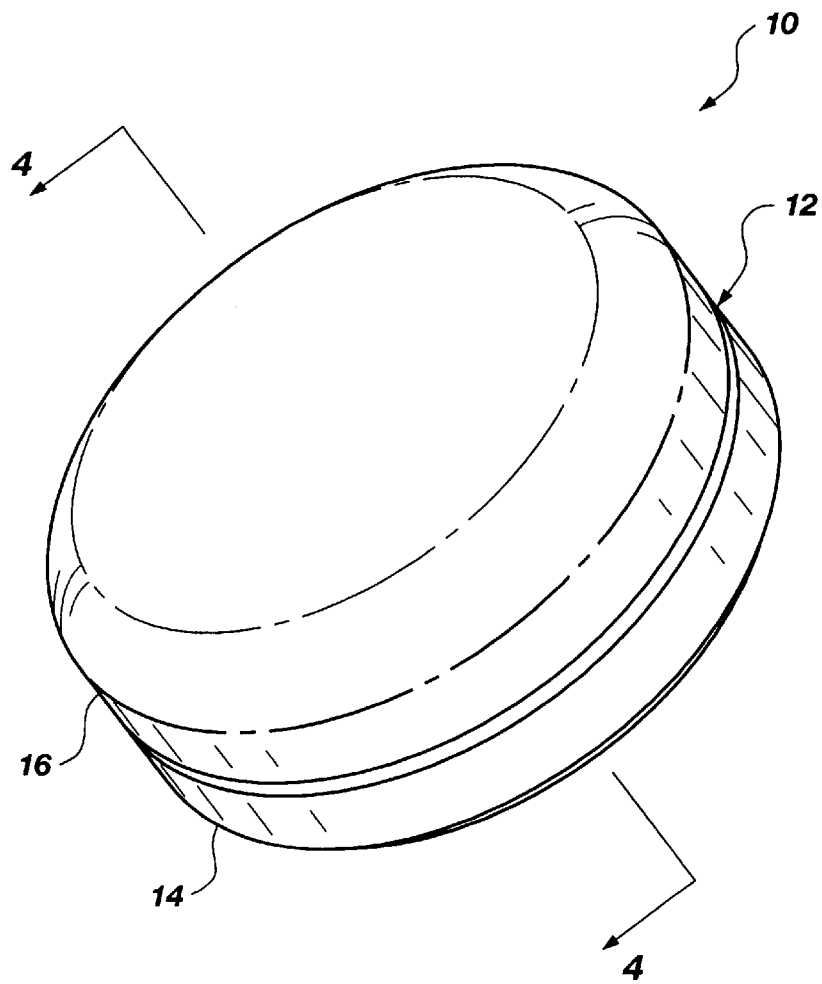
FIG. 1 shows a perspective view of a preferred embodiment of the wrist support device of the present invention.
Figure 2:
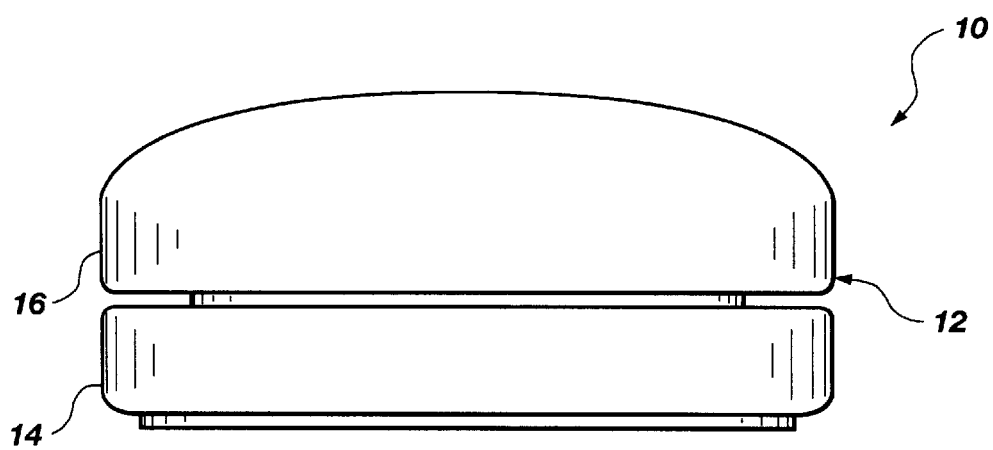
FIG. 2 shows a side elevational view of the preferred embodiment of the wrist support device of the present invention.

Referring to FIGS. 1 and 2, there is shown a perspective view of one embodiment of a wrist support device, generally indicated at 10, made in accordance with the principles of the present invention. The wrist support device 10 has a wrist support body 12. The wrist support body 12 is modular, having a separate lower portion 14 removably attached to an upper portion 16.

Figure 3:
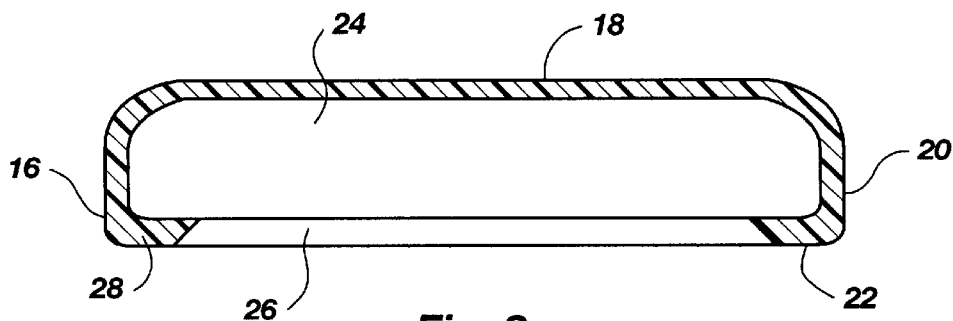
FIG. 3 shows a cross sectional view of the preferred embodiment of an upper portion of the wrist support device of the present invention taken along line 3—3 of FIG. 1.

Referring to FIG. 3, the upper portion 16 is typically formed of a resilient shell having an upper surface 18, an annular perimeter wall 20 which extends downwardly from the upper surface, a bottom 22, and an interior cavity 24.

Figure 4:
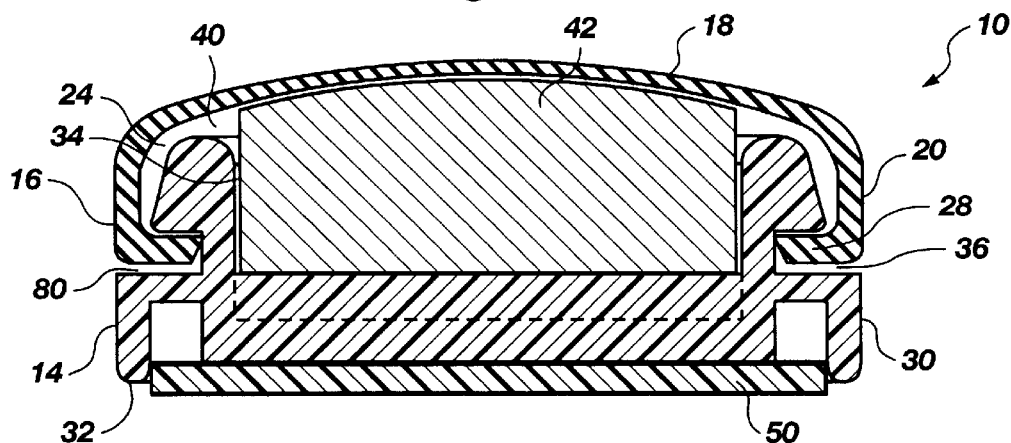
FIG. 4 shows a cross sectional view of the preferred embodiment of the wrist support device of the present invention taken along line 3—3 of FIG. 1.
Figure 6:
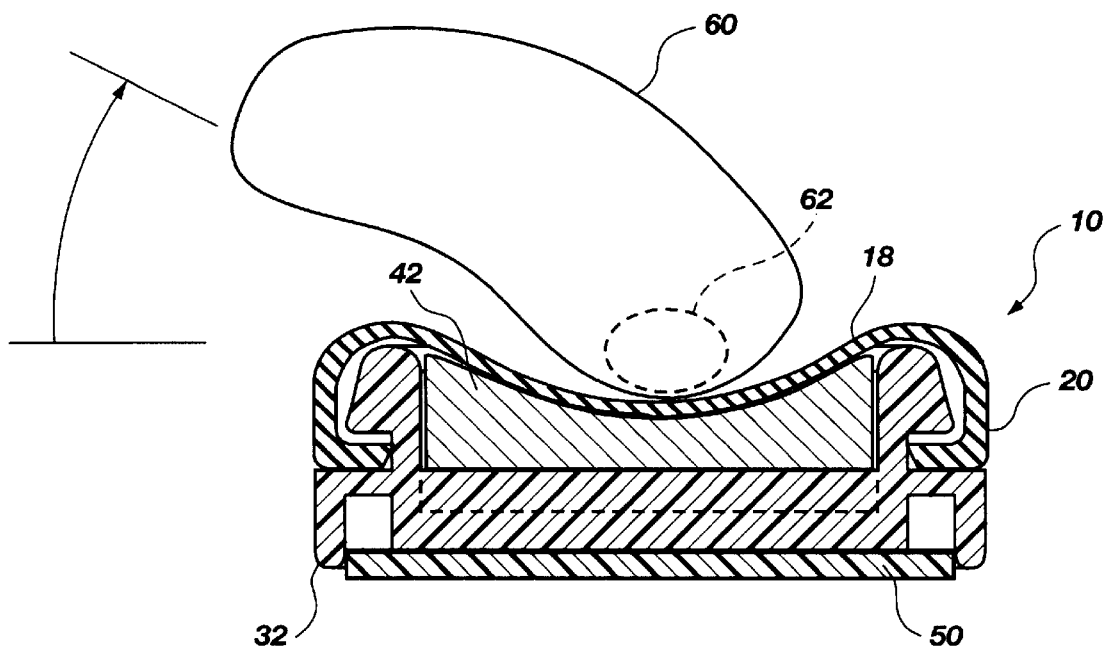
FIG. 6 shows a cross sectional view of the preferred embodiment of the wrist support device of the present invention engaged by a wrist of a user.

The upper surface 18 is typically formed by a flexible and resilient, plastic material, such as polypropylene, which has a high coefficient of friction with human skin. The upper surface 18 flexibly moves between a convex orientation, as shown in FIG. 4, and a concave orientation, as shown in FIG. 6. When in a relaxed or unused state, the upper surface 18 is generally biased in the convex orientation. The convex shape of the upper surface 18 cushions the wrist of the user.

After prolonged contact of the wrist with the upper surface 18, a natural adhesion may occur due to sweat or oils. The aforementioned convex shape of the upper surface 18 also facilitates separation between the upper surface and the user's wrist when the wrist is lifted from the upper surface by pushing away from the wrist. In addition, the convex shape of the upper surface 18 peels away from the generally curved shape of the wrist, thus reducing the surface area at which the upper surface and wrist have contact.

Figure 5:
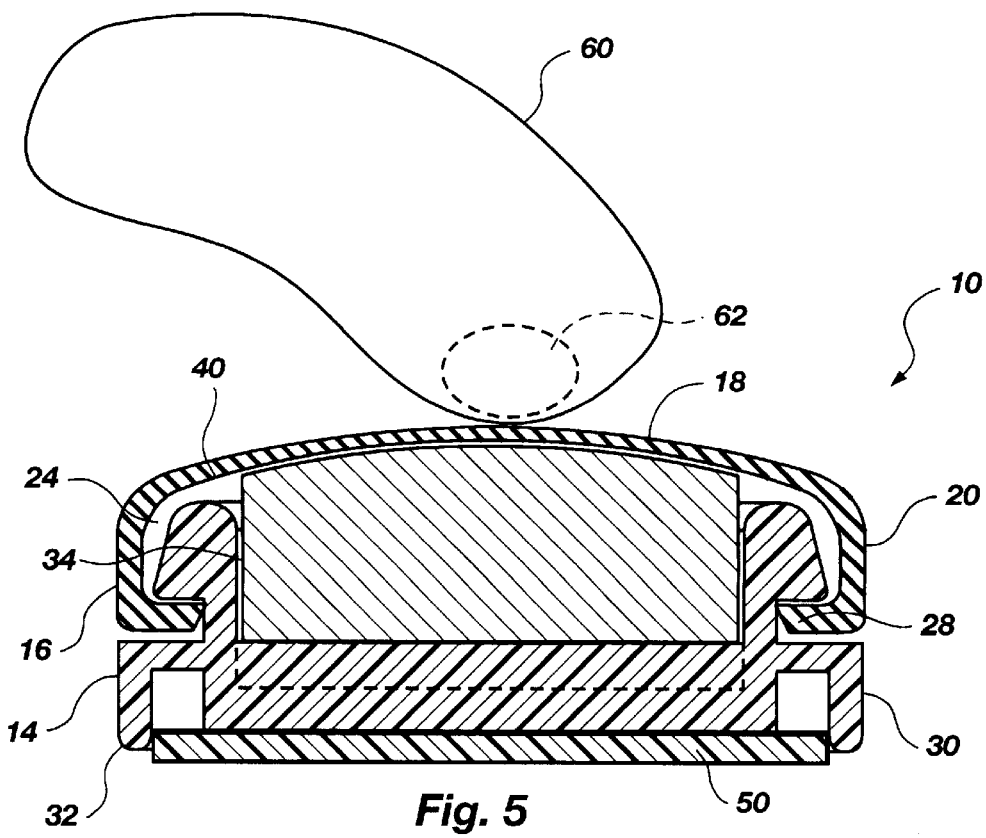
FIG. 5 shows a cross sectional view of the preferred embodiment of the wrist support device of the present invention being initially engaged by the wrist of a user.

Referring to FIG. 5, when a wrist or hand is placed on the upper surface 18, the upper surface will generally model or deform slightly to conform to the curvatures of the wrist or hand. The perimeter wall 20 surrounds the upper surface 18 and biases the wrist into a more natural and laterally inclined orientation. Such a positioning of the pisiform holds the hand in a comfortable, natural position which places less stress on the soft tissue of the wrist than previous wrist supports. This position results in a reduction in tension within the soft tissue of the wrist and a decrease in fatigue by those using the device 10. In addition, the perimeter wall 20 nests the pisiform bone of the wrist into the approximate center of the upper surface 18. The perimeter wall 20 is preferably higher than the upper surface when engaged by the wrist to bias and nest the wrist. In addition, the perimeter wall 20 is preferably stiff with respect to the upper surface 18 to bias and nest the wrist.

An additional advantage of forming the shell of the upper portion 16 out of polypropylene or a vinyl material is that the shell, and in particular the upper surface 18, can be easily cleaned with conventional cleaning materials. By cleaning the upper portion often, the transmission of diseases, both those of the skin and those commonly transferred by the hands, can be avoided. Additionally, odors which can develop due to bacterial growth can be eliminated.

For ease of manufacture, the perimeter wall 20 and the bottom 22 are also typically formed of a material similar to that used for the upper surface 18. Numerous different vinyls and similar materials can be used to provide an appropriate blend of flexibility and frictional interaction with human skin.

Referring again to FIG. 3, the bottom 22 of the upper portion 16 has an opening 26. The bottom 22 surrounding the opening 26 forms a flange or lip 28.

Figure 8:
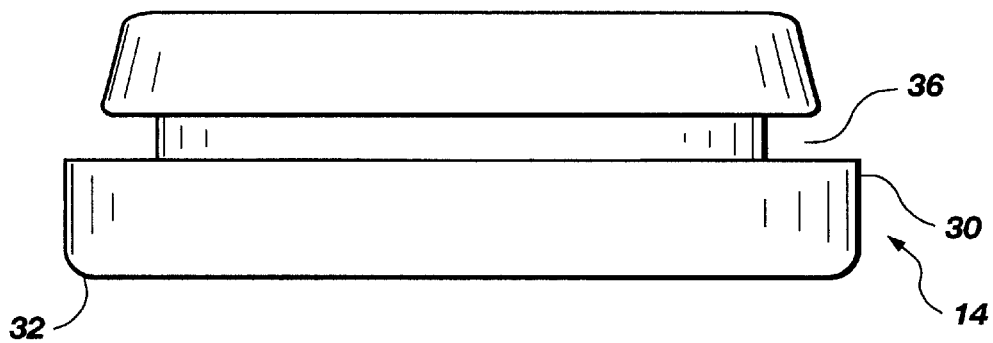
FIG. 8 shows a side elevational view of the preferred embodiment of a lower portion of the wrist support device of the present invention.
Figure 9:
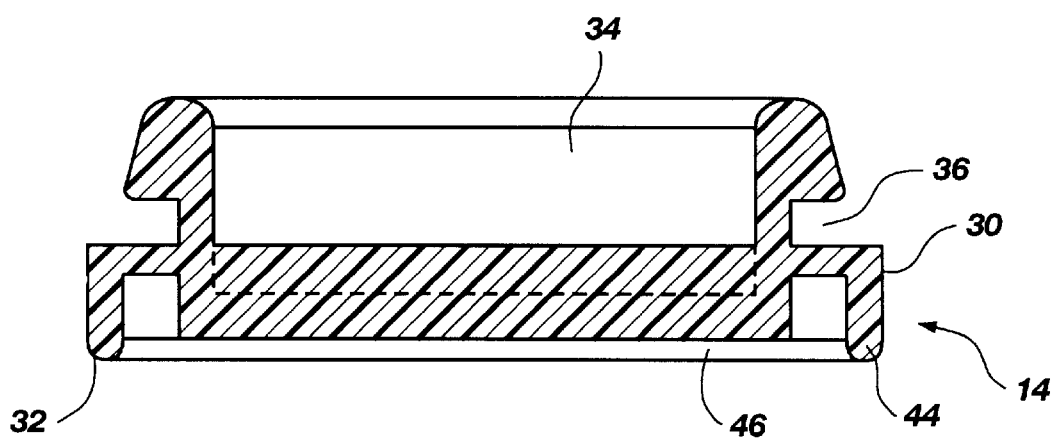
FIG. 9 shows a cross sectional view of the preferred embodiment of the lower portion of the wrist support device of the present invention.

Referring to FIGS. 8 and 9, the lower portion 14 has an annular perimeter wall 30, a lower surface 32, and a cavity 34, as shown in FIG. 9. An annular notch 36 is formed around the perimeter wall 30 of the lower portion 14. Referring again to FIG. 4, a portion of the perimeter wall 30 of the lower portion 14 is received within the cavity 24 of the upper portion 16. The notch 36 of the lower portion mates with the flange 28 of the upper portion 16 attaching the lower portion to the upper portion.

The lower portion 14 is typically formed by a hard, plastic material, but may also be formed of the same material as the upper portion.

Referring again to FIG. 4, the cavity 34 of the lower portion 14 and the cavity 24 of the upper portion 16 unite to form a cavity 40 within the body 12. A cushion 42 is disposed in the cavity 40 formed by the upper and lower portions 16 and 14. The cushion 42 cushions the wrist and causes the upper surface 18 to form a convex portion, biasing the upper surface in a convex orientation. The cushion 42 is preferably a compressible foam material. Because the maximum compressibility of the cushion 42 typically occurs in the middle, a hand/wrist position which most people find comfortable to use with the device 10 is to place the skin overlying the pisiform in the center of the upper surface 18, as shown in FIG. 6. The perimeter wall 20 of the upper portion 14 naturally orients or biases the wrist into the center of upper surface 18.

Referring again to FIG. 9, the lower surface 32 of the lower portion 14 has a flange 44 formed around its perimeter. The flange 44 forms an indentation 46 which receives a glide mechanism 50 and helps position the glide mechanism on the lower surface 32, as shown in FIG. 4.

Referring again to FIG. 4, the glide mechanism 50 is attached to the lower surface 32 of the lower portion 14. The glide mechanism 50 is typically made of a piece of material, preferably felt, which is slightly smaller in diameter than the diameter of the lower portion 14. The slide mechanism 50 should extend across a majority of the lower surface of the lower portion to prevent the lower portion from catching on the surface and prevent continued sliding.

Those skilled in the art will appreciate that the glide mechanism need not be one continuous piece. For example, four smaller pieces of felt could be placed adjacent the sidewall at the perimeter of the lower surface 32.

The glide mechanism enables the device to slide across surfaces and to be used with keyboards, a mouse, ten-keys, and the like.

Alternatively, the glide mechanism 50 may be a thin layer of a hard, low friction plastic layer, such as EVA. The plastic layer allows the wrist support device 10 to slide on high friction materials, such as neoprene. Those familiar with computers will recognize that neoprene and similar materials are commonly used for "mouse" pads. Thus, the hard plastic layer allows the support device 10 to slide.

Additionally, the wrist support device 10 may be provided with multiple lower portions 14, one with a glide mechanism 50 for use with low friction surfaces and the other for use with high friction surfaces. Because the lower portion is removably attachable to the upper portion, the multiple lower portions may be interchanged to suit the intended use. When the wrist support device 10 is to be used on a neoprene pad or other high friction material, the lower portion 14 with the plastic layer could be attached to the upper portion. When the wrist support device 10 is to be used on a desk or other low friction surface, the lower portion 14 with the felt pad could be attached to the upper portion.

Alternatively, the glide mechanism 50 may be removably disposed in the indentation 46. The glide mechanism 50 may be held in place by a friction between the glide mechanism 50 and the flange 44. In this manner, different glide mechanisms may be easily and quickly snapped in and out.

Referring now to FIG. 6, there is shown a cross-sectional view of the wrist support device 10, and a figure representing the normal position the wrist 60 at the base of a human hand (as opposed to the soft tissue between the wrist bones and the radius and ulna). When a human hand is placed on a horizontal planar support surface, it is usually most comfortable for the wrist to be positioned at an incline of between about 10 and 30 degrees as shown. If the hand is placed flat on the planar support surface, the elbow must either be rotated outwardly or the pressure within the wrist will cause fatigue within a short period of time.

Those who routinely use a computer keyboard for prolonged periods of time generally find that efforts to keep their elbows rotated outwardly sufficiently to relieve stress in the wrist results in fatigue in the arms and upper back. The present invention solves these concerns by encouraging or biasing the wrist 60 to stay in its natural position. As the wrist 60 is placed on the upper surface 18 of the upper portion 16, the small bone which extends downwardly from the wrist, i.e. the pisiform 62, nests into the upper portion 16 at approximately the center of the upper surface. Thus, rather than turning the wrist 60 into an unnatural position, the upper portion 16 helps to maintain a comfortable wrist orientation.

The projection of the skin adjacent the pisiform 62 into the upper surface 18 of the upper portion 16, causes the wrist support device 10 to move with the hand and wrist 60 of the user. Thus, for example, if the user must enter numbers from a 10-key pad at the far end of the computer keyboard, the user's right hand may be slid down to the 10-key pad without moving the left hand and without lifting the right hand/wrist off the support device 10. With the elongate pad of the prior art, repeated movements without lifting the hand/wrist would cause irritation to skin as the skin rubbed along the bar with each move.

By providing two supports, the present invention also allows the user to move both hands independently. Thus, to reach a key at the back of the key board, the left had may be moved forward with the wrist support device 10, while the right hand is being moved rearwardly on another wrist support device, or vice-versa. By allowing independent movement without the need to lift each hand from the support, the present invention significantly decreases the overall strain on the user's arms and hands.

The embodiment shown in FIGS. 1 through 10 is substantially round. While it is believed that most wrist support devices 10 made in accordance with the present invention will be round due to cost and ease of manufacture, numerous other shapes may be used.

Figure 10:
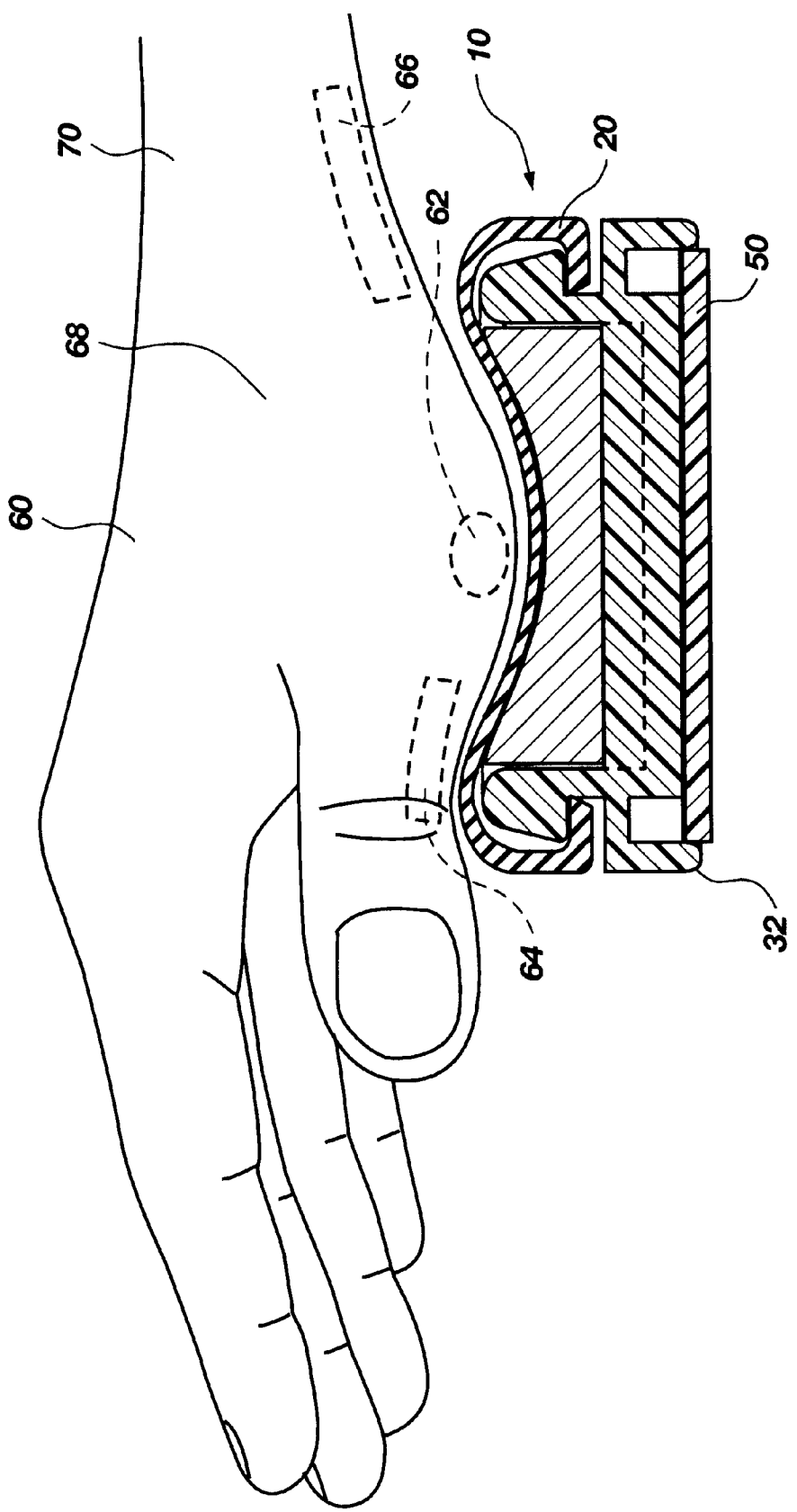
FIG. 10 shows a cross sectional view of the preferred embodiment of the wrist support device of the present invention engaged by a wrist of a user.

Referring to FIG. 10, when the upper portion 16 of the support device 10 is positioned under the bones of the wrist 60 so that the projection caused by the pisiform 62 contacts an approximate center of the upper surface 18, the outer edge of the upper portion 16, as represented by the perimeter wall 20, extends forward to a position beneath the outermost metacarpal bone 64 (which is attached to the small finger). The upper portion 16 also extends rearwardly to a position adjacent the end of the ulna 66. However, because of the projection formed by the pisiform 62, the outer edge of the upper portion 16 supports these areas rather than placing a significant amount of pressure on them. If the hand or arm must be rotated forwardly or rearwardly, the upper portion 16 allows the movement and helps encourage or bias the hand or arm back to the original position. Thus, the user's hand is always encouraged into a position which causes the least amount of stress.

By spreading support throughout the bones of the wrist 60, the metacarpal bone 64, and the ulna 66, very little pressure is placed on the soft tissue 68 between the bones of the wrist 60 and the lower arm 70. Thus, the device 10 significantly decreases fatigue in the user and greatly decreases the risk of repetitive stress disorders such as carpal tunnel syndrome. It also prevents the projection formed by the pisiform 62 from developing sore areas due to prolonged forceful contact with hard surfaces such as desks.

As shown in FIG. 4, the upper surface 18 of the upper portion 16 has a convex portion. The curvature assists the user in finding the proper position for the wrist by feel, rather than requiring the user to look at the wrist support device 10 each time the user's hands are removed. Thus, a user may repeatedly remove his or her hands from the devices to perform other tasks, and then properly position the devices when typing is recommenced. To properly facilitate placement of the area about the pisiform in the center of the upper surface, the upper portion should be substantially 2⅜ inches in diameter. This size allows the upper surface to be large enough so that the pisiform may be positioned near the center of the device without the need to exactly position the wrist.

Referring again to FIG. 4, a gap 80 is advantageously formed between the upper and lower portions 16 and 14 around a periphery of the device 10. The gap 80 allows the upper portion 16 to move with respect to the lower portion 14. Thus, the upper portion 16 is also advantageously movably attached to the lower portion 14. In a relaxed state, or when not in use, the upper portion 16 is biased in an upper position, as shown in FIG. 4. When the device 10 is engaged by the wrist 60 of a user, the upper portion 16 moves from the upper position to a lower position, as shown in FIG. 5. As the upper portion 16 moves, the flange 28 moves with the notch 36 of the lower portion 14.

The gap 80 is preferably between 1/16 and ¼ of an inch. The gap 80 should be Large enough for the upper portion to move a significant distance, but small enough so that the device is not too thick.

The movement of the upper portion 16 from the upper position to the lower position provides an initial stage of cushion as the wrist 60 engages the upper surface 18 of the device 10. The cushion 42 and air inside the cavity 40 resist the movement of the upper portion 16 between the upper and lower positions. As the upper portion 16 moves towards the lower portion 14, air is gradually released from the cavity 40 through the gap 80. The gradual release of air from the device aids the cushion in providing the initial stage of cushioning.

The wrist of the user will often engage the device with a certain small degree of velocity, or with a certain small degree of impact. The gap 80 permits the upper portion 16 to move or give in response to this impact force, thus adding another aspect of comfort to using the device.

As the wrist 60 of the user continues to engage the device 10, the upper surface 18 moves from the convex orientation and the concave orientation, as shown in FIG. 6. This movement of the upper surface 18 provides a secondary stage of cushioning. As described above, this movement of the upper surface 18 is resisted by the cushion 42 and by air inside the cavity 40. Just as the initial stage of cushioning was in response to the impact force of initial contact, the secondary stage of cushioning is in response to the weight of the hand and wrist. Therefore, the device provides a range of various cushioning stages to provide additional comfort.

Figure 7:
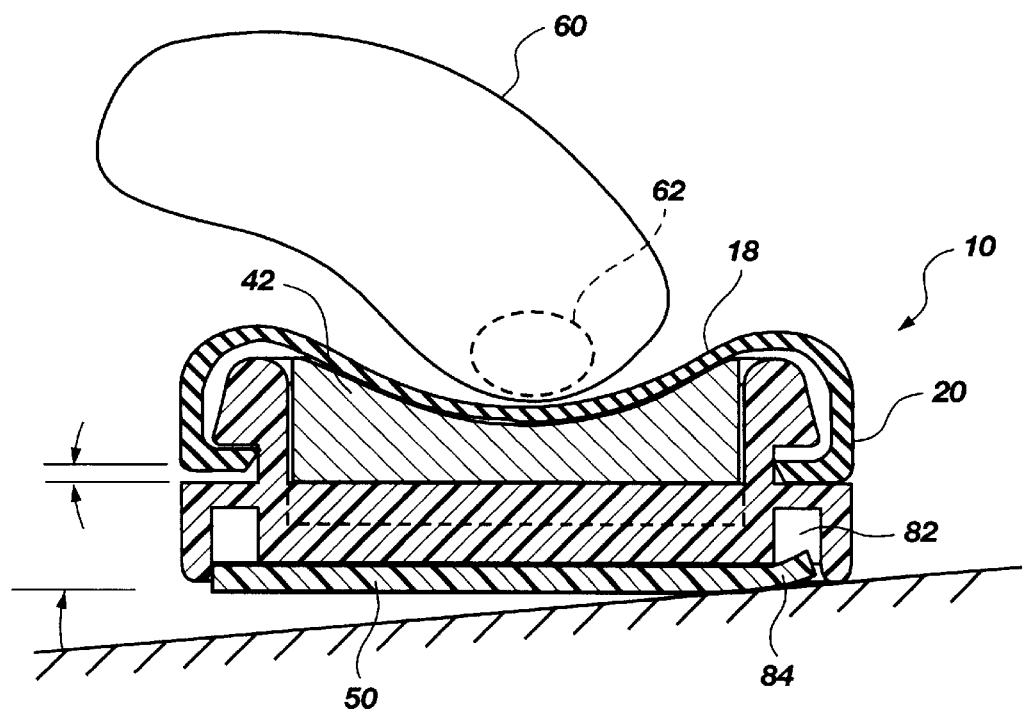
FIG. 7 shows a cross sectional view of the preferred embodiment of the wrist support device of the present invention being engaged by the wrist of a user.

Referring to FIG. 7, the gap 80 allows the upper portion 16 to pivot with respect to the lower portion 14. Thus, the upper portion 16 is also advantageously pivotally attached to the lower portion 14. As the hand of the user moves, the wrist 60 pivots or rotates with respect to the surface. The gap 80 allows the upper portion 16 to pivot a small degree with the wrist to provide additional comfort, without compromising the device's ability to bias the wrist and hand into the proper orientation.

In addition, the wrist 60 of the user will often engage the upper surface 18 without the pisiform exactly nesting in the center. The pivoting upper portion 16 provides a degree of forgiveness with respect to the positioning of the pisiform on the upper surface. Therefore, the upper portion 16 will pivot in order to correct for the pisiform being located slightly off-center.

A channel 82 is formed about a periphery in the lower surface 32 of the lower portion 14. The channel 82 receives an edge 84 of the glide mechanism 50 when the glide mechanism is bent. As the wrist 60 of the user pivots or rotates, the edge 84 of the glide mechanism 50 bends into the channel 82. The channel 82, and the bending of the edge 84 of the glide mechanism 50 into the channel, allows the lower portion 14 to pivot a small degree with respect to the surface. Therefore, the pivot of the lower portion combined with the pivot of the upper portion provide a small degree of flexibility and pivot to the device for added comfort.

Furthermore, the gap 80 allows air to enter and escape from the cavity 40 within the device 10. Thus, the gap 80 between the upper and lower portions 16 and 14 allows the air to equalize within the device 10. Therefore, the device 10 may provide acceptable cushioning at various elevations and even within aircraft.

Figure 11:
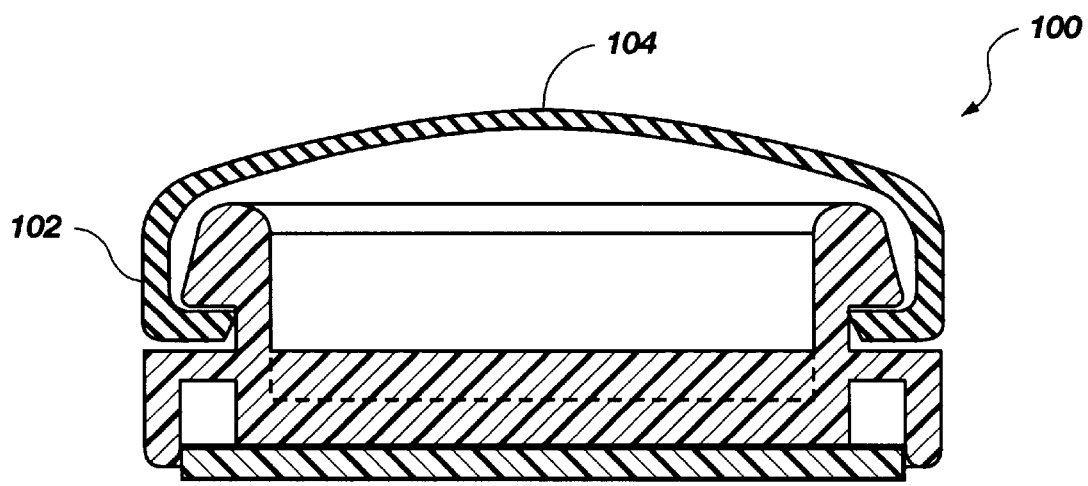
FIG. 11 shows a cross sectional view of an alternative embodiment of the wrist support device of the present invention.

Referring to FIG. 11, there is shown an alternative embodiment of a wrist support device, generally indicated at 100. The alternative embodiment is similar to the preferred embodiment in most respects except that the cushion of the preferred embodiment has been eliminated in the alternative embodiment. The device 100 has an upper portion 102 with an upper surface 104 that has been formed to have a convex shape in a relaxed or unused state. Rather than being biased in the convex orientation by a cushion as in the preferred embodiment, the upper portion 102 is formed so that the material of the upper portion causes it to be biased in the convex orientation, such as by molding a resilient plastic material to form a convex shape.

Figure 12:
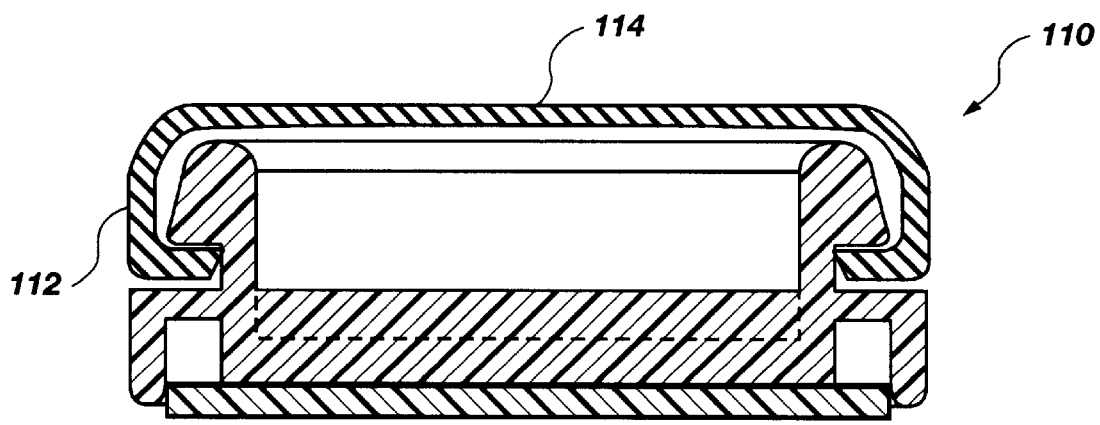
FIG. 12 shows a cross sectional view of an alternative embodiment of the wrist support device of the present invention.

Referring to FIG. 12, there is shown an alternative embodiment of a wrist support device, generally indicated at 110. The alternative embodiment is similar to the preferred embodiment in most respects except that the upper portion of the alternative embodiment has a generally non-convex orientation. The device 110 has an upper portion 112 with an upper surface 114 that has been formed to have a generally non-convex, i.e. planar or concave, shape in a relaxed or unused state. The upper surface still flexibly moves to a concave orientation to bias and nest the pisiform, as in the preferred embodiment. In addition, the lower portion is still removably attachable to the upper portion so that lower portions with different glide mechanisms may be attached to the upper portion to suit the intended use. The device 110 may or may not have a cushion disposed in a cavity formed between the upper and lower portions. A disadvantage of the illustrated planar surface 114 is an attendant visual perception of greater hardness or stiffness as compared to the "pillowed" convex structure 104 of FIG. 11.

Thus there is disclosed an improved wrist support device. Those skilled in the art will appreciate that numerous modifications can be made without departing from the scope and spirit of the invention. The appended claims are intended to cover such modifications.

What is claimed is:

1. A wrist support device for preventing repetitive stress disorders in a wrist of a user as the wrist and bones contained therein move above a planar support surface, the device comprising:

a wrist support body having a flexible and resilient upper surface, a lower surface, and a perimeter wall, the upper surface including means for flexibly moving between a convex orientation when in a relaxed state and a concave orientation when engaged by a projection in the user's wrist formed by a pisiform bone, the upper surface being biased in the convex orientation to cushion the wrist and facilitate separation from natural adhesion by prolonged contact between the upper surface and the user's wrist, the perimeter wall surrounding the upper portion including means for biasing the wrist into a laterally inclined orientation and nesting the pisiform bone into the approximate center of the upper surface;

gliding means disposed on the lower surface for facilitating movement of the wrist support body along the planar surface; and a flange formed around a perimeter of the lower surface to form an indentation in which the gliding means is disposed.

2. The wrist support device of claim 1, wherein the wrist support body has an interior cavity and a cushion disposed in the interior cavity of the wrist support body causing the upper surface to bias in the convex orientation.

3. The wrist support device of claim 1, further comprising a channel formed about a periphery of the lower surface of the wrist support body to receive an edge of the gliding means to permit the wrist support body to pivot with respect to the planar support surface.

4. The wrist support device of claim 1, wherein the wrist support body comprises an upper portion movably attached to a lower portion, the upper portion moving between an upper position and a lower position and being biased in the upper position to cushion the wrist upon initial contact between the wrist and the upper surface.

5. The wrist support device of claim 1, wherein the wrist support body comprises an upper portion pivotally attached to a lower portion, the upper portion pivoting with respect to the lower portion.

6. The wrist support device of claim 1, wherein the wrist support body comprises an upper portion, a lower portion, and a gap formed between the periphery of the upper and lower portions.

7. The wrist support device of claim 6, wherein the gap is between approximately $\frac{1}{32}$ and $\frac{1}{4}$ of an inch.

8. The wrist support device of claim 1, wherein the wrist support body is round and has a diameter of approximately between 2¼ and 2½ inches.

9. A modular wrist support device for preventing repetitive stress disorders in a wrist of a user as the wrist and bones contained therein move above a planar support surface, the device comprising:

an upper portion having an upper surface and a perimeter wall, the upper surface defining at least a concave portion therein when engaged by a projection in the user's wrist formed by a pisiform bone, the perimeter wall surrounding the upper surface including means to bias the wrist into a laterally inclined orientation and to nest the pisiform bone into the approximate center of the upper surface;

a separate lower portion removably and pivotally attached to the upper portion and having a bottom, the upper surface pivoting with respect to the lower portion to facilitate rotation of the wrist and provide additional comfort; and gliding means disposed on the bottom of the lower portion for facilitating movement of the upper and lower portions along the planar surface.

10. The wrist support device of claim 9, wherein the upper surface defines a convex portion therein when in a relaxed state and flexibly moves between a convex and a concave orientation and wherein the upper surface is biased in the convex orientation when in the relaxed state.

11. The wrist support device of claim 9, wherein the upper portion has an interior cavity and a cushion disposed in the interior cavity of the upper portion causing the upper surface to form a convex portion when in a relaxed state.

12. The wrist support device of claim 9, wherein the upper portion has an interior cavity, a bottom with an opening, and a flange formed around the opening; and wherein the lower portion has a notch formed around a perimeter wall, the interior cavity of the upper portion receiving a portion of the perimeter wall of the lower portion, the flange of the upper portion mating with the notch of the lower portion to removably attach the lower portion to the upper portion.

13. The wrist support device of claim 9, wherein the bottom of the lower portion has a receiving means formed therein for receiving the gliding means.

14. The wrist support device of claim 13, wherein the receiving means comprises a flange formed around a perimeter of the bottom of the lower portion to form an indentation in which the gliding means is disposed.

15. The wrist support device of claim 9, further comprising a channel formed about a periphery of the bottom of the lower portion for receiving an edge of the gliding means to permit the lower portion to pivot with respect to the planar support surface to facilitate rotation of the wrist and to provide additional comfort.

16. The wrist support device of claim 9, wherein the upper portion is movably attached to the lower portion, the upper portion moving between an upper position and a lower position and being biased in the upper position to cushion the wrist upon initial contact between the wrist and the upper surface.

17. The wrist support device of claim 9, further comprising a gap formed between the upper portion and the lower portion when in a relaxed state.

18. The wrist support device of claim 17, wherein the gap between the upper and lower portions is between approximately 1/32 and 1/4 of an inch.

19. The wrist support device of claim 9, wherein the upper portion is round and has a diameter of approximately between 2¼ and 2½ inches.

20. A modular wrist support device for preventing repetitive stress disorders in a wrist of a user as the wrist and bones contained therein move above a planar support surface, the device comprising:

an upper portion having an upper surface, interior cavity, and a perimeter wall, the upper surface including means for flexibly moving between a convex orientation when in a relaxed state and a concave orientation when engaged by a projection in the user's wrist formed by a pisiform bone, the upper surface being biased in the convex orientation to cushion the wrist and facilitate separation from natural adhesion by prolonged contact between the upper surface and the user's wrist, the perimeter wall surrounding the upper surface including means to bias the wrist into a laterally inclined orientation and to nest the pisiform bone into the approximate center of the upper surface;

a separate lower portion attached to the upper portion and having a bottom; and gliding means disposed on the bottom of the lower portion for facilitating movement of the upper and lower portions along the planar surface; and wherein the upper portion has a bottom with an opening and a flange formed around the opening; and wherein the lower portion has a notch formed around a perimeter wall, the interior cavity of the upper portion receiving a portion of the perimeter wall of the lower portion, the flange of the upper portion mating with the notch of the lower portion to removably attach the lower portion to the upper portion.

21. The wrist support device of claim 20, wherein the upper portion is movably attached to the lower portion, the upper portion moving between an upper position and a lower position.

22. The wrist support device of claim 20, wherein the upper portion is pivotally attached to the lower portion, the upper portion pivoting with respect to the lower portion.

23. The wrist support device of claim 20, wherein the lower portion has a flange formed around a perimeter of the bottom of the lower portion to form an indentation in which the gliding means is disposed.

24. The wrist support device of claim 20, wherein the bottom of the lower portion has a channel formed about its periphery for receiving an edge of the gliding means to permit the lower portion to pivot with respect to the planar support surface.

25. The wrist support device of claim 20, further comprising a gap of variable length formed between the upper and lower portions, said variable length being represented by (i) a biased position wherein the length is at its largest value occurring when in a state of non-use with the upper member at maximum height, and (ii) a compressed position wherein the length is reduced in response to weight applied to the upper member by a user's hand.

26. A wrist support device for preventing repetitive stress disorders in a wrist of a user as the wrist and bones contained therein move above a planar support surface, the device comprising:

a wrist support body having a flexible and resilient upper surface, a lower surface, and a perimeter wall, the upper surface including means for flexibly moving between a convex orientation when in a relaxed state and a concave orientation when engaged by a projection in the user's wrist formed by a pisiform bone, the upper surface being biased in the convex orientation to cushion the wrist and facilitate separation from natural adhesion by prolonged contact between the upper surface and the user's wrist, the perimeter wall surrounding the upper portion including means for biasing the wrist into a laterally inclined orientation and nesting the pisiform bone into the approximate center of the upper surface;

gliding means disposed on the lower surface for facilitating movement of the wrist support body along the planar surface; and a channel formed about a periphery of the lower surface of the wrist support body to receive an edge of the gliding means to permit the wrist support body to pivot with respect to the planar support surface.

27. The wrist support device of claim 26, further comprising a flange formed around a perimeter of the lower surface to form an indentation in which the gliding means is disposed.

28. The wrist support device of claim 26, wherein the wrist support body comprises an upper portion pivotally attached to a lower portion, the upper portion pivoting with respect to the lower portion.

29. The wrist support device of claim 26, wherein the wrist support body comprises an upper portion, a lower portion, and a gap formed between the periphery of the upper and lower portions; and wherein the gap is between approximately 1/32 and 1/4 of an inch.

30. The wrist support device of claim 26, wherein the wrist support body comprises an upper portion attached to a lower portion; wherein the upper portion has an interior cavity, a bottom with an opening and a flange formed around the opening; and wherein the lower portion has a notch formed around a perimeter wall, the interior cavity of the upper portion receiving a portion of the perimeter wall of the lower portion, the flange of the upper portion mating with the notch of the lower portion to removably attach the lower portion to the upper portion.

* * * * *